United States Patent [19]

Foster et al.

[11] Patent Number: 5,120,655

[45] Date of Patent: Jun. 9, 1992

[54] RIBOFLAVIN PRODUCING STRAINS OF MICROORGANISMS

[75] Inventors: Edward W. Foster, Loveland, Co; Dale C. Gyure, Fort Collins, Co; Donald L. Heefner, Longmont; Craig A. Weaver, Louisville; Michael J. Yarus; Linda A. Burdzinski, both of Boulder, all of Colo.

[73] Assignee: Zeagen, Inc., Broomfield, Colo.

[21] Appl. No.: 57,948

[22] Filed: Jun. 5, 1987

Related U.S. Application Data

[63] Continuation-in-part of Ser. No. 811,234, Dec. 20, 1985, abandoned.

[51] Int. Cl.$^5$ .................... C12N 1/16; C12N 15/00; C12P 15/00
[52] U.S. Cl. .................... 435/255; 435/66; 435/172.1
[58] Field of Search ............ 435/85, 86, 119, 255, 435/921, 172.1, 911, 944, 66; 935/84

[56] References Cited

U.S. PATENT DOCUMENTS

| | | | |
|---|---|---|---|
| 2,363,227 | 11/1944 | Burkholder | 435/66 |
| 2,411,445 | 11/1946 | Maizel | 435/66 |
| 2,424,003 | 7/1947 | Tanner | 435/66 |
| 2,667,445 | 1/1954 | Hickey | 435/66 |
| 3,433,707 | 3/1969 | Matsubayashi et al. | 435/66 |

FOREIGN PATENT DOCUMENTS

| | | | |
|---|---|---|---|
| 84109683 | 8/1984 | European Pat. Off. | |
| 0137226 | 4/1985 | European Pat. Off. | 435/66 |
| 108767 | 12/1984 | German Democratic Rep. | |
| 608833 | 6/1978 | U.S.S.R. | |

OTHER PUBLICATIONS

Gerhardt et al., "Manual of Methods for General Bacteriology" Am. Soc. Microbiol. 1981.
Sikyta, B., "Methods in Industrial Microbiology" J. Wiley 1983.
Olczyk, C., "N-Alkanesasa substratum for riboflavin production 1. Investigations of the dynamics of the flavinogenesis in chosen yeasts of the genus Candida", Pol. J. Pharmacol. Pharm. vol. 30, pp. 83–88, 1978.
Lodder, J. "The Yeasts" 1970 N. Holland Publishing Co.
Perlman, "Primary Products of Metabolism", Microbiology 1978.
Straube, et al., "The Influence of Iron Concentration and Temperature on Growth and Riboflavin Overproduction of *Candida guilliermondii*" Biotechnology and Bioengineering Symposium No. 4, 225–31 (1973).
Chopde, et al., "Factors Influencing Riboflavin Synthesis by Cytophaga Hutchinsonii" Indian J. of Microbiology, vol. 20, No. 2 (1980).
Schlee, et al., "Physiology and Biochemistry of Riboflavin Formation" Die Pharmazie, No. 12 (1984).
Goodwin, "Production and Biosynthesis of Riboflavin in Micro-Organisms" Process in Industrial Microbiology.
Baruah, "Isolation and Characterization of Yeasts and Bacteria Producing Riboflavin from Petroleum Hydrocarbons" Indian J. of Experimental Biology, vol. 16(10) pp. 1113–1115 (1978).
Borzani, "Kinetics of Nitrogen Consumption During the Batch Growth of *Candida guilliermondii* on Diesel Oil and on Molasses", Biotechnology Letters, vol. 6, No. 8, pp. 511–516 (1984).
Bresler, et al., "Riboflavin Bio-Synthesis Operon in *Bacillus subtilis*" translated from Genetika, vol. 14, No. 12, pp. 2082–2090 (1978).
Goodwin, et al., "Studies on the Biosynthesis of Riboflavin" Biochemistry, vol. 57, pp. 631–641.
Brown, et al., "Studies on the Biosynthesis of Riboflavin" Biochemistry, vol. 61, pp. 37–46.

*Primary Examiner*—Douglas W. Robinson
*Assistant Examiner*—Irene Marx
*Attorney, Agent, or Firm*—Sheridan, Ross & McIntosh

[57] ABSTRACT

Strains of yeast of the species *Candida famata* are disclosed which can produce 10 grams of riboflavin per liter in 6 days, and in particular, strains identified by ATCC Accession Nos. 20849 and 20850. Riboflavin yields of more than 20 grams per liter in 200 hours have been achieved. Strains of the present invention have increased sensitivity to iron inhibition of flavinogenesis and have enhanced riboflavin production per cell at increased iron concentrations in the fermentation medium.

2 Claims, No Drawings

5,120,655

RIBOFLAVIN PRODUCING STRAINS OF MICROORGANISMS

REFERENCE TO CO-PENDING APPLICATION

This application is a continuation-in-part application of the commonly assigned U.S. patent application Ser. No. 06/811,234 filed Dec. 20, 1985, now abandoned.

FIELD OF THE INVENTION

The present invention is directed toward microorganisms having the ability to produce high amounts of riboflavin and, in particular, to strains of the yeast *Candida famata* producing increased amounts of riboflavin and methods for fermentation of the microorganisms. The invention is further directed toward methods for selecting riboflavin overproducers.

BACKGROUND OF THE INVENTION

Riboflavin is synthesized by a wide variety of microorganisms in amounts which greatly exceed the metabolic requirements of the organisms. Ascomycetes, such as *Ashbya gossypii* and *Eremothecium ashybii* are known for production of riboflavin by fermentation. Typically, riboflavin produced by these organisms is used as a feed additive.

Riboflavin production by other microorganisms is also known. For example, the bacteria belonging to the genera Clostridium and Bacillus, as well as various genera of yeast, including Candida, Saccharomyces, Hansenula, and Pichia are known for riboflavin production. More specifically, for example, U.S. Pat. No. 3,433,707 (1969) to Matsubayashi, et al. describes the production of riboflavin by three species of Pichia yeast. Yields of riboflavin of between 10.5 mg/l and 51 mg/l in 12 days were reported. Riboflavin over-production by *Ashbya gossypii* of 6.42 g/l has been reported by Szczesniak et al. (1973) as discussed in Perlman, *Primary Products of Metabolism*. 2 Econ. Microbiology, at 312 (1978).

Commonly assigned United States patent application Ser. No. 061,811,234 filed Dec. 20, 1985, reports the development of strains of *Candida famata* having increased riboflavin production. The strains of *C. famata* discussed in Ser. No. 061,811,234 produced 5 grams of riboflavin per liter in six days of fermentation.

Study of the metabolic requirements of riboflavin producing yeast have reported a riboflavin production sensitivity to concentrations of iron. For example, Straube, et al., *The Influence of Iron Concentration and Temperature on Growth and Riboflavin Overproduction of Candida guilliermondii*, Biotechnology and Bioengineering Symposium No. 4, 225-231 (1973) reports that iron concentrations of $10^{-5}$M almost completely inhibit the production of riboflavin and that riboflavin production is approximately inversely proportional to the iron concentration. Straube, et al. also found that the presence of cobalt can reverse the riboflavin production inhibition effect of iron. At cobalt concentrations of $10^{-4}$M and iron concentration of $10^{-5}$M, the same amount of riboflavin was produced as when no cobalt was present and iron was limited to $10^{-7}$M.

Other references discuss iron sensitivity in riboflavin producing microorganisms and, in particular, that iron sensitivity can be partially overcome by addition of cobalt, zinc, or chelating agents to the fermentation medium. Chopde, et al., *Factors Influencing Riboflavin Synthesis by Cytophaga Hutchinsonii*, Indian J. of Microbiology, v. 20 n.2 (1980); Schlee, et al., *Physiology and Biochemistry of Riboflavin Formationashybii*, Die Pharmazie, No. 12, (1984).

While iron inhibits riboflavin production, it has also been reported that increased amounts of iron stimulate cell growth. Therefore, yeast having decreased sensitivity to iron inhibition of flavinogenesis should produce high amounts of riboflavin because higher cell densities can be achieved by increasing iron concentrations.

Strains of riboflavin producing microorganisms having decreased sensitivity of riboflavin production to the presence of iron have been reported. Russian Patent No. SU 330189 (abstract); German Patent No. DD 108767 (abstract).

Accordingly, there is a need for microorganisms having improved levels of riboflavin production. There is a further need for strains of flavinogenic microorganisms having resistance to iron inhibition of riboflavin production. Additionally, there is a need for improved methods for selecting riboflavin over-producing microorganisms. There is also a need for fermentation media supporting increased cell growth and flavinogenesis. The microorganisms of the present invention produce riboflavin in amounts which are greatly in excess of wild type strains of flavinogenic microorganisms and which are highly improved over yields of known developed strains.

SUMMARY OF THE INVENTION

The present invention is directed to strains of the yeast *Candida famata* which can produce 10 grams of riboflavin per liter in six days. Riboflavin yields of more than 20 grams per liter in 200 hours have been achieved. *C. famata* strains A and B, identified, respectively, by ATCC Accession Nos. 20849 and 20850, are the most flavinogenic strains of the present invention. The strains identified by ATCC Accession Nos. 20849 and 20850 have been deposited with ATCC under the terms of the Budapest Treaty. In another embodiment, the present invention involves strains of *C. famata* having decreased sensitivity to iron inhibition of flavinogenesis. Such strains have the characteristic of enhanced riboflavin production per cell at increased iron concentrations in the fermentation medium. Developed strains of *C. famata* have also been selected for resistance to inhibition of growth by depleted media and by deoxyglucose.

In a further embodiment, the instant invention involves a process for selecting improved microorganisms which are resistant to inhibition of growth by depleted medium. Such microorganisms have the ability to grow to higher cell densities to produce larger amounts of metabolic products. This process first involves producing a depleted media by growing a population of microorganisms until cell growth stops. The microorganisms are then removed from the medium to form a depleted medium. A selection medium is then formed which comprises the depleted medium. A second population of microorganisms is then subjected to mutagenesis and introduced to the selection medium. Strains of the mutated population having the ability to grow on the depleted medium are selected. Preferably, the second population of microorganisms is of the same species as the first population which formed the depleted media and more preferably, the same strain.

In a still further embodiment, the present invention involves a process for selecting microorganisms producing high amounts of riboflavin. This process involves mutating a starting population of microorganisms. The mutated population is then cultured on a nutrient medium which includes the antibiotic tubercidin which presumably inhibits purine metabolism. The tubercidin is present in the nutrient medium at concentrations effective to inhibit colony formation by some of the microorganisms in the mutated population. Microorganisms having the ability to form colonies on the tubercidin medium are then selected. Such microorganisms can then be tested for riboflavin overproduction. This selection process has been found to select for riboflavin overproducers.

Another embodiment of the present invention includes a process for producing riboflavin by culturing strains of microorganisms of the present invention in a fermentation medium. Increased riboflavin production can be attained by iron concentrations in the medium of between about 5.4 $\mu$M and about 15 $\mu$M. The fermentation medium also includes glycine in concentrations up to about 7 g/l. The fermentation is conducted by maintaining nutrient concentrations in the medium and other fermentation conditions to support cell growth and riboflavin production. After cell growth levels off, riboflavin is recovered from the fermentation medium.

DETAILED DESCRIPTION

Strains of riboflavin producing yeast of the species C. famata have been developed which produce improved levels of riboflavin. Yields of more than 10 grams of riboflavin per liter of medium in 144 hours are routinely attained, and yields of more than 20 grams of riboflavin per liter in 200 hours have been achieved. The strains of the present invention are thirty to forty times more flavinogenic than wild type C. famata and three and one-half times more flavinogenic than the highest previously known riboflavin producer.

In particular, strain A, ATCC Accession No. 20849, can produce more than 20 grams of riboflavin in a 200 hour fermentation run. Various strains have been developed from strain A which are more flavinogenic than strain A as measured in a 2 ml roll tube riboflavin assay. This assay, which is described in detail in the Example Section, is not designed for maximizing riboflavin yield, but is used for comparison of flavinogenesis between strains of organisms under identical conditions. Strain B, ATCC Accession No. 20850, was developed from strain A and is fifty percent more flavinogenic than strain A in the roll tube assay.

Strains of the C. famata in the present invention have decreased sensitivity to iron inhibition of riboflavin synthesis. As discussed above, it has been reported that iron is an inhibitor of riboflavin synthesis in many microorganisms, and in particular, in species of the yeast Candida. Increased iron in the fermentation medium has been found to increase not only cell growth of the C. famata strains of the present invention, but also riboflavin production per cell weight. While riboflavin would be expected to increase with increased cell growth from high iron concentrations, the riboflavin increases which are observed are greater than what would be expected from increased cell growth alone. Accordingly, flavinogenesis in the iron resistant strains of the present invention is not only insensitive to iron inhibition, but is stimulated by higher iron concentrations on a per cell basis.

Stimulation of riboflavin production for iron resistant strains of C. famata in the present invention has been detected at iron concentrations of about 3.6 micromolar ($\mu$M). Above concentrations of about 16.1 $\mu$M, however, iron tends to inhibit riboflavin synthesis of even these strains. During fermentation, it is preferred to have iron molar concentrations of between about 5.40 $\mu$M and about 15 $\mu$M, more preferably between about 6.12 $\mu$M and about 12 $\mu$M, and most preferably between about 9.8 $\mu$M and about 10.8 $\mu$M.

Another important metabolic characteristic of strain A and its progeny is a resistance to inhibition of growth and riboflavin production in fermentation medium in which a culture has been grown to a terminal cell density. Such a medium is termed a "depleted medium". Such resistance allows production of higher riboflavin yields by achieving higher cell densities. These strains have also been found to produce increased yields of riboflavin on a per cell basis.

Discussion of the instant invention is made herein with reference to the yeast C. famata. C. famata is also known as Toruloosis candida. The methods and processes of the present invention, however, are equally applicable to other species of Candida and other riboflavin overproducing yeast and microorganisms. Accordingly, specific reference to C. famata is not intended to limit the scope of the invention to this particular species.

According to the present invention, improved riboflavin producing strains of microorganisms are selected by processes of mutating a culture of microorganisms and selecting strains having improved characteristics for riboflavin production. Typically, mutated microorganisms are cultured on solid medium containing some inhibitory compound. Colonies which form in the presence of the inhibitor are cultured and tested for riboflavin production. Strains of microorganisms having high riboflavin production are then selected.

The mutagenesis of cultures of microorganisms can be conducted by any of various means known in the art, and can include either chemical or physical mutagenesis. For example, chemical mutagens suitable for the present invention include, but are not limited to N-methyl-N'-nitro-N-nitrosoguanadine, diepoxybutane, ethylmethane sulfonate, mustard compounds, hydrazine, and nitrous acid. Physical mutagens can include, but are not limited to, ultraviolet and gamma radiation. A starting culture is subjected to a mutagenic agent at an intensity sufficient to leave a particular size surviving population. The size varies between mutagens and depends on the amount of mutations a mutagen induces in the surviving population at a given kill rate. For example, the desired kill rate for NTG should leave approximately 10%-50% of the starting population. Nitrous acid mutagenesis should leave approximately 0.01% to 0.1% of the starting population and ultraviolet mutagenesis should leave approximately 1.0%. Cells treated in this manner are harvested, washed, and suspended in a non-growth-supporting medium, such as physiological saline. Such cells can then be subjected to one or more selection processes.

A number of intermediate strains of riboflavin overproducing strains of C. famata have been selected in the development of strains A and B using selection processes described below. Strain C, ATCC Accession No. 20755, was developed by a number of selection procedures from wild type C. famata and is described in Ser. No. 06/811,234. Strain C is a predecessor to strains described below, including A and B. Strain C can produce 1.1 g/l of riboflavin in 7 days in the 2 ml roll tube assay. Using strain C as a starting population, a glucose analog selection process was conducted to select for riboflavin overproducers.

According to the present invention, riboflavin overproducers can be selected by selecting microorganisms which are resistant to analogs of glucose. Such strains of microorganisms are likely to be more efficient at accumulating glucose, at converting glucose to riboflavin, or at overcoming glucose repression. Accordingly, a starting culture of riboflavin producing microorganisms is mutated in the manner described above. The mutated population is then plated on medium containing inhibitory concentrations of glucose analogs or mixtures thereof. Viable colonies from the plated mutated cells are selected for resistance to inhibition by glucose analogs. These colonies are then tested for riboflavin production.

The concentration of the glucose analog is dependent upon several factors, including the inhibitory effect of the analog and the starting sensitivity of the culture to inhibition of riboflavin production by the analog. Typically, a minimum inhibitory concentration experiment is conducted to determine the minimum concentration at which the analog inhibits growth in the unmutated starting population. This minimum concentration is generally the concentration used for the selection process, however it should be recognized that higher concentrations can be used up to a concentration at which even growth of resistant mutants is inhibited. When 2-deoxyglucose is the glucose analog, concentrations of between about 700 $\mu$g/ml and about 1500 $\mu$g/ml, more preferably between about 700 $\mu$g/ml and about 1000 $\mu$g/ml, and most preferably between about 700 $\mu$g/ml and about 800 $\mu$g/ml, are desirable.

Strain D was selected by the glucose analog selection process in which strain C was the starting population which was mutated and selected from. Strain D can produce 1.58 g/l of riboflavin in 7 days in the 2 ml roll tube assay. This strain was used as a starting population for an iron sensitivity selection process to select for riboflavin overproducers.

As discussed above, it has been reported that riboflavin production is inhibited by small amounts of iron. It has now been recognized that it would be desirable to develop a riboflavin producing strain of microorganism having a decreased sensitivity to iron inhibition because the strain could be cultured in a medium having high iron concentration which could support increased cell growth.

To select for riboflavin producers having decreased sensitivity to iron, a culture of microorganisms is mutated in the manner discussed above. The resulting culture is spread onto solid medium containing assimilable sources of carbon, nitrogen, and inorganic elements in the presence of high iron concentrations. For example, a suitable medium is YMG Medium (see Table 1) supplemented with 2.23% glycine. The mutated cells are grown on this medium at a temperature suitable for riboflavin production. Mutants without increased resistance to iron inhibition of riboflavin production form white or cream-colored colonies because riboflavin is not overproduced. However, mutant colonies with increased resistance to inhibition of riboflavin production by iron are yellow due to the presence of riboflavin. Such yellow colonies can be tested for high riboflavin overproducers.

TABLE 1

| YMG Medium | |
|---|---|
| Yeast extract | 3 g/l |
| Malt extract | 3 g/l |
| Peptone | 5 g/l |
| Carbon source (2%) | 20 g/l |

The iron concentration in the selection process is dependent, among other factors, upon the iron sensitivity of the starting population. For example, if the iron sensitivity process were to be conducted on a starting population of wild-type *C. famata*, the iron concentration for selection would be less than if the starting population was a strain of *C. famata* which had already been selected for decreased sensitivity to iron inhibition of riboflavin production. As discussed above with regard to the glucose analog selection, an iron concentration is typically selected by a minimum inhibitory concentration experiment. According to the present invention, iron molar concentrations of between about 5 $\mu$M and about 50 $\mu$M and more preferably between about 10 $\mu$M and about 30 $\mu$M and most preferably between about 16 $\mu$M and about 20 $\mu$M are effective for selecting for decreased iron sensitivity.

Strain E was selected by the iron sensitivity process with strain D as the starting population. Strain E can produce 1.70 g/l of riboflavin in 7 days in the 2 ml roll tube assay. This strain was used as a starting population for a depleted media selection process to select for riboflavin overproducers.

Riboflavin overproducers can be selected by resistance to growth inhibition on a depleted medium. It is known that in closed biological systems, such as laboratory yeast cultures, cell growth and production of biological products eventually ceases, even in the presence of excess nutrients. While the reasons for cessation of cell growth and riboflavin production in *C. famata* are not known, it is believed that three reasons are, at least partially, responsible for this phenomena. It is thought that most organisms are inefficient at using trace nutrients below a given concentration. Therefore, as such trace nutrients are depleted to a given concentration, growth is inhibited. The second possible reason is that during the growth and riboflavin production phases, substances are produced as by-products which are inhibitory to further growth and riboflavin production. A third possible reason is that high concentrations of fed or unused media components may repress growth. This selection process is directed toward selection of microorganisms which are capable of growing and producing riboflavin on depleted media. It is believed that such microorganisms are more efficient at utilizing trace nutrients at low levels and/or are resistant to inhibitory or repressive compounds produced during growth and riboflavin production phases. Such selected organisms are valuable because, for a given starting medium and fermentation conditions, cell growth and riboflavin production continues for a longer period of time to produce higher yields of riboflavin production.

According to the depleted media selection process, depleted media is prepared by growing an initial culture of microorganisms until cell growth stops or levels off, and more preferably until late stationary phase. It is preferred that the depleted media be prepared by culturing the same species, and preferably, the same strain, of microorganism that is to be selected in the selection step. While any microorganism depletes trace nutrients and produces inhibitory compounds, selection is most effective if the mutated population which is selected is subject to the same environmental stresses from the depleted media which caused the initial population to stop growing. If the initial population is different from the mutated population, growth in the initial population can be limited by depletion of trace minerals or production of inhibitory or repressive compounds which may not stress the mutated population.

After growth and production of products in the initial culture stops, cells are removed from the culture to form depleted media. Separation can be conducted by various means known to those skilled in the art. For example, cells can be removed from the medium by centrifugation. Alternatively, cells can be removed by ultra-filtration.

A selection media is prepared using the depleted media as described above. Sources of carbon, nitrogen, and inorganic nutrients can be added to the depleted media to form a selection media for the selection of depleted media resistant strains. The amount and type of nutrients to be added to the depleted media can vary. By way of example, a carbon and a nitrogen source, such as sucrose and glycine, can be added to the depleted medium. Alternatively, the depleted medium can be mixed in varying proportions with a nutrient media, such as 4B medium (See Table 2). The relative proportions of depleted media and nutrient media can be determined by conducting a minimum inhibitory concentration experiment and using the lowest level of depleted media which inhibits growth in an unmutated population.

TABLE 2

| 4B Medium | |
|---|---|
| $KH_2PO_4$ | 0.5 g/l |
| $MgSO_4.7H_2O$ | 0.2 g/l |
| urea | 1.84 g/l |
| sucrose | 60 g/l |
| D-biotin | 1 ug/l |
| $H_3BO_4$ | 20 ug/l |
| $MnSO_4$ | 20 ug/l |
| $ZnSO_4$ | 140 ug/l |
| $CuSO_4$ | 20 ug/l |
| $Na_2MoO_4$ | 20 ug/l |

The selection process is conducted by subjecting a starting population of riboflavin producing microorganisms to mutagenesis in the manner described above to form a mutated population. The mutated population is introduced to the depleted media selection medium. Typically, microorganisms which do not have an increased resistance to inhibition by depleted medium are not viable on the selection medium. Colonies which form on the depleted media selection medium are selected for having increased resistance to depleted media. The selected colonies are then tested for riboflavin production.

458 Strain A was selected by the depleted media selection process with strain E as the starting population. Cells were removed from the initial culture to form the depleted media by centrifugation. The depleted media was sterilized and any remaining cells were removed by filtration with a 0.5 micron membrane filter. The selection media was formed by adding sucrose and glycine to the supernatant. Strain A can produce 2.5 g/l of riboflavin in the roll rube assay. An additional depleted media selection process was conducted using strain A as the starting population.

This second depleted media selection process produced strain F which can produce 3.4 g/l of riboflavin in 7 days in the 2 ml roll rube assay. In this selection process, cells were removed from the depleted media by filtration on a 0.5 micron membrane filter and the selection media was formed with fifty percent depleted media and fifty percent 4B medium. Strain F was used as the starting population for a selection process using tubercidin as a selection agent.

Another selection process for riboflavin over-producers selects microorganisms which are resistant to inhibition of growth by purine analogs, and in particular, tubercidin. Such compounds presumably inhibit purine metabolism, and since purines are precursors to riboflavin, such compounds interfere with production of riboflavin. Many known purine analogs have been used for the study of purine metabolism, however, no known reference has reported successful use of purine analogs for selection of riboflavin overproducers. Further, no known reference reports the use of tubercidin for the study of purine metabolism or for selection of riboflavin overproducers.

It has been determined that strains of riboflavin producing microorganisms which grow and produce riboflavin in the presence of tubercidin can have an improved ability to produce riboflavin. Such tubercidin resistant strains either have the ability to make increased levels of purines or the ability to make purines more efficiently. According to this selection process, a culture of riboflavin producing microorganisms is mutated as described above. The surviving population is plated on medium containing assimilable sources of carbon, nitrogen, and inorganic elements in the presence of tubercidin. From the plated populations, viable colonies are selected. These colonies are then tested for riboflavin production.

The concentration of tubercidin used in the present selection process is dependent upon various factors, including the sensitivity of the starting population to inhibition. As discussed above, a suitable concentration can be determined by conducting a minimum inhibition concentration experiment in which the lowest concentration of tubercidin which inhibits growth in an unmutated population is determined. It should be recognized that higher concentrations of tubercidin can be used up to a concentration which inhibits growth of even resistant mutants. While the concentration of tubercidin can vary, the concentration in the selection process is typically between about 85 $\mu g/ml$ tubercidin and about 200 $\mu g/ml$ tubercidin, more preferably between about 85 $\mu g/ml$ tubercidin and about 150 $\mu g/ml$ tubercidin, and most preferably between about 85 $\mu g/ml$ tubercidin and about 115 $\mu g/ml$ tubercidin.

Strain B was selected by the tubercidin selection process with strain F as the starting population. Strain B can produce 3.8 g/l of riboflavin in 7 days in the 2 ml roll tube assay. Strain G was also selected by the tubercidin selection process with strain A as the starting population. The riboflavin production capacity of strain G is 2.9 g/l in 7 days in the 2 ml roll tube assay. Strain G was used as a starting population for an ultraviolet light sensitivity selection process.

The various selection methods described above select for overproducers of riboflavin by introducing a mutated population of riboflavin producing microorganisms to a medium which inhibits riboflavin production in some manner. In addition to selecting microorganisms having high production rates of riboflavin, it is desirable to obtain a riboflavin overproducer having stable riboflavin production rates. The specific strains of *C. famata* of the present invention have been derived from the product of a cell-cell fusion procedure which was conducted prior to development of strain C as described in Ser. No. 811,234. Cell fusion products have multiple copies of chromosomes, parts of which are likely to be lost over time by rearrangement of genes due to their redundancy. Cell fusion products which were selected for riboflavin overproduction are highly likely to have multiple copies of genes for riboflavin production. The capacity to overproduce can be easily lost if such organisms are unstable genetically. It is therefore desirable to select overproducers of riboflavin having a decreased ability for chromosomal rearrangement.

In bacteria and *Saccharomyces cerevisiae*, mutants have been obtained that are defective in the ability to rearrange their DNA. Clark, et al., *Proc. Natl. Acad. Sci. USA*, 53:451 (1965); Mazza, et al., *Microbiologica*, 1:111 (1978); Haynes, et al., *The Molecular Biology of the Yeast Saccharomyces*, Cold Spring Harbor Laboratory, 371 (1981). Some types of these mutants can be obtained by selecting for increased sensitivity to mutagens such as ultraviolet light. Strains of riboflavin overproducing microorganisms, and particularly cell fusion products which are selected for sensitivity to ultraviolet light, are believed to possess an increased degree of stability for riboflavin production.

The ultraviolet light sensitive selection process is conducted by subjecting a starting population of microorganisms to mutagenesis, as described above. The cell suspensions are plated onto a medium, for example, YMG medium, at a dilution to yield between about 100 and about 400 colonies per plate, and more preferably between about 150 and about 200 colonies per plate. After the colonies become visible, colony patterns are replicated twice to fresh agar plates. Colonies having a diameter of between about 0.5 mm diameter and about 1.0 mm diameter are visible. The first replica is exposed open-faced to ultraviolet light at an intensity which is sub-lethal to non-mutagenized cells. An appropriate level of ultraviolet light can be determined by subjecting colonies of non-mutagenized cells to various doses of ultraviolet light and determining a level which does not kill cells. For a non-mutagenized culture of *C. famata*, a sublethal level of ultraviolet light is between about 5 joules per square meter ($J/m^2$) and about 20 $J/m^2$, and more preferably between about 10 $J/m^2$ and about 15 $J/m^2$. The irradiated replica and non-irradiated replica are incubated to allow for colony formation. The irradiated plate must be kept in the dark to prevent visible light from reversing the effect of the ultraviolet light. Visible light has an established effect of repairing genetic damage caused by irradiation. After the colonies become visible, the irradiated replica is compared with the non-irradiated plate for colonies present on the non-irradiated plate which are absent on the irradiated plate. In this manner, colonies are identified having increased sensitivity to ultraviolet light.

Strain H was selected by the ultraviolet sensitivity selection process with strain G as the starting population. Strain H has a riboflavin production capacity of 3.1 g/l in 7 days in the 2 ml roll tube assay.

Riboflavin can be produced by fermentation of strains A and B and other microorganisms selected by the processes described above. It will be apparent to those skilled in the art that higher riboflavin yields can be achieved with a culture of a particular strain if the culture is substantially free from contamination by microorganisms of a lower riboflavin producing strain. Such biologically pure cultures can be produced by forming a culture from one microorganism of the desired strain.

The riboflavin production by strains A and B and microorganisms selected by the processes described above can vary when different fermentation media and procedures are used. While many fermentation procedures are known to those in the art, a fermentation medium and process have been developed which produce consistently high growth rates and riboflavin production. The preferred fermentation medium for production of riboflavin by strains A and B is listed in Table 3.

TABLE 3

| Compound | Concentration |
|---|---|
| | (g/l) |
| glucose | 60.0 |
| glycine | 4.60 |
| urea | 3.68 |
| $KH_2PO_4$ | 1.00 |
| $MgSO_4$ | 0.72 |
| | (mg/l) |
| $CoSO_4.7H_2O$ | 11.8 |
| $CuSO_4.5H_2O$ | 0.020 |
| $H_3BO_3$ | 0.020 |
| $(NH_4)_6Mo_7O_{24}$ | 0.140 |
| $MnSO_4$ | 0.020 |
| $ZnSO_4.7H_2O$ | 17.0 |
| $FeSO_4.7H_2O$ | 2.0 |
| biotin | 0.0118 |

All medium constituents except glucose are filter sterilized into the vessel. Glucose (630 g/l) is autoclaved 30 minutes at 121° C. and 15 psi. The initial fermentor volume in a 14 liter fermentor is 10.5 liters. The pH of the medium is adjusted to 6.9-7.0 prior to inoculation.

Generally, the medium includes sources of carbon, nitrogen, phosphates, sulfates, magnesium, potassium, iron, and other trace metals. The concentrations provided in Table 3 represent initial concentrations of components and not minimum concentrations which must be maintained during the fermentation. It should be recognized that some components cannot be provided initially in sufficiently high quantities to last throughout the entire fermentation. For such components, the fermentation medium must be monitored and minimum concentrations maintained.

While glucose is listed as the preferred carbon source in the present fermentation medium, other carbon sources can perform equally well. For example, sucrose and fructose are suitable for the medium. Additionally, other non-sugar carbon sources, such as some alcohols, are suitable. The initial concentration of glucose in the fermentation medium should be between about 45 g/l and about 60 g/l, more preferably between about 50 g/l and about 60 g/l, and most preferably between about 55 g/l and about 60 g/l.

The fermentation medium also includes glycine. Glycine is a critical component of the fermentation medium for effective riboflavin production. While glycine is essential for riboflavin production, excess amounts of glycine inhibit growth of *C. famata*. At concentrations greater than about 7 g/l, cell growth stops. At very low concentrations of glycine, on the order of about 0.5 g/l, glycine is depleted rapidly from the fermentation medium. Acceptable initial glycine concentrations are between about 2 g/l and about 6 g/l, more preferably between about 4 g/l and about 6 g/l, and most preferably between about 4 g/l and about 5 g/l.

Nitrogen is provided to the fermentation medium to support growth by the addition of urea. The initial concentration of urea in the fermentation medium should be between about 2 g/l and about 9 g/l, more preferably between about 3 g/l and about 7 g/l, and most preferably between about 3 g/l and about 5 g/l. Other sources of nitrogen are suitable for use in the present fermentation medium. Optimal concentrations of such other sources can be determined by running test fermentations at varying concentrations of the nitrogen source while holding other variables constant and determining the highest riboflavin production.

Phosphate is provided to the fermentation medium by the addition of monobasic potassium phosphate ($KH_2PO_4$). $KH_2PO_4$ is initially provided to the fermentation medium at concentrations of between about 0.5 g/l and about 2.0 g/l, more preferably between about 0.75 g/l and about 1.5 g/l, and most preferably between about 0.85 g/l and about 1.15 g/l. In addition to phosphate, $KH_2PO_4$ provides potassium to the fermentation medium. Potassium is required for growth, however, at concentrations providing sufficient phosphate, the potassium which is added is far in excess of the nutritional requirements of the culture. While phosphate can be added in other forms, such as sodium phosphate, potassium phosphate is preferred because the potassium nutritional requirement is fulfilled.

The fermentation medium also includes magnesium sulfate ($MgSO_4$) as a source of sulfate. The initial fermentation medium contains this compound at concentrations between about 0.5 g/l and about 1.0 g/l, more preferably between about 0.6 g/l and about 0.8 g/l, and most preferably between about 0.65 g/l and about 0.75 g/l. While the fermentation culture has a nutritional magnesium requirement, at these concentrations, the magnesium provided is far in excess of the requirement. The sulfate can also be added in compounds other than magnesium sulfate.

The fermentation medium also includes a number of sources of trace minerals, including cobalt, copper, boron, molybdenum, manganese, zinc, and iron. The fermentation medium has nutritional requirements for each of these elements, and at the initial concentrations of the trace mineral containing compounds, these requirements are easily met and require no further additions during the fermentation process. While many of the trace minerals are provided as sulfates, the amount of sulfate added by these compounds is not significant to the overall sulfate requirements of the fermentation.

Cobalt is provided to the fermentation medium in the form of heptahydrate cobalt sulfate ($CoSO_4.7H_4O$). The initial concentration of this compound is between about 10 mg/l and about 13 mg/l, more preferably between about 11 mg/l and about 12 mg/l, and most preferably between about 11.5 mg/l and about 12 mg/l. Cobalt also has the beneficial effect of competing with iron to reduce any inhibitory effect of iron on riboflavin synthesis.

Copper is added to the fermentation medium in the form of pentahydrate copper sulfate $CuSO_4.5HO$). This compound is initially provided to the fermentation medium at concentrations between about 0.015 mg/l and about 0.025 mg/l, more preferably between about 0.017 mg/l and about 0.023 mg/l, and most preferably between about 0.018 mg/l and about 0.022 mg/l. Copper also has the effect of competing with iron to reduce any inhibitory effect of iron on riboflavin synthesis.

Zinc is added to the fermentation medium in the form of heptahydrate zinc sulfate ($ZnSO_4.7H_2O$). This compound is initially provided to the fermentation medium at concentrations between about 15 mg/l and about 20 mg/l, more preferably between about 16 mg/l and about 19 mg/l, and most preferably between about 16 mg/l and about 18 mg/l. Zinc is also a competitor for iron and reduces any inhibitory effect of iron on riboflavin synthesis.

The fermentation medium also includes a source of iron, heptahydrate iron sulfate ($FeSO_4.7H_2O$), to meet the nutritional iron requirements of the fermentation. The initial concentration of this compound in the fermentation medium is between about 1.5 m/l and about 4.0 mg/l, more preferably between about 1.7 mg/l and about 3.0 mg/l, and most preferably between about 1.9 mg/l and about 2.3 mg/l.

Boron is provided to the fermentation medium in the form of boric acid ($H_3BO_3$). Boric acid is provided to the initial fermentation medium at concentrations of between about 0.015 mg/l and about 0.025 mg/l, more preferably between about 0.017 mg/l and about 0.023 mg/l, and most preferably between about 0.019 mg/l and about 0.021 mg/l. Boron can be provided to the fermentation medium in other forms provided that the boron is in a form which is biologically available to the cells and in a non-toxic form.

Molybdenum is provided to the medium in the form of ammonium molybdate (VI) (($NH_4)_6Mo_7O_{24}$). This compound is provided in concentrations between about 0.12 mg/l and about 0.16 mg/l, more preferably between about 0.13 mg/l and about 0.15 mg/l, and most preferably between about 0.135 mg/l and about 0.145 mg/l.

Manganese is provided to the fermentation medium in the form of manganese sulfate ($MnSO_4$) This compound is provided in a concentration of between about 0.015 mg/l and about 0.025 mg/l, more preferably between about 0.017 mg/l and about 0.023 mg/l, and most preferably between about 0.019 mg/l and about 0.021 mg/l.

The fermentation medium also includes biotin, a vitamin which is required by yeast generally. This vitamin is provided in concentrations above about 0.005 mg/l, more preferably above about 0.009 mg/l, and most preferably above about 0.0118 mg/l.

As discussed above, during the fermentation, some of the components of the medium are depleted. It is preferable to initiate fermentation with relatively high concentrations of such components so that growth is supported for a period of time before additions are required. The preferred ranges of these components are maintained throughout the fermentation by making additions as levels are depleted by fermentation. Levels of components in the fermentation medium can be monitored by, for example, sampling the fermentation medium periodically and assaying for concentrations. Alternatively, once a standard fermentation procedure is developed, additions can be made at timed intervals corresponding to known levels at particular times throughout the fermentation. As will be recognized by those in the art, the rate of consumption of nutrients increases during fermentation as the cell density in the medium increases.

Glucose, glycine, urea, and phosphate concentrations in the fermentation medium are monitored during the fermentation. The glucose concentration in the medium is monitored and maintained between about 20 g/l and about 60 g/l, more preferably between about 20 g/l and about 40 g/l, and most preferably at about 30 g/l. These concentrations of glucose can be maintained in the fermentation medium by the addition of a concentrated glucose feed having a concentration of about 600 g/l.

The concentration of glycine in the fermentation medium is also monitored and maintained between about 1 g/l and about 7 g/l, more preferably between about 2 g/l and about 5 g/l, and most preferably at about 3 g/l. The glycine concentration can be controlled by the addition of a concentrated glycine feed having a concentration of about 200 g/l.

The concentration of urea in the fermentation medium is also monitored and maintained at concentrations of between about 1 g/l and about 9 g/l, more preferably between about 2 g/l and about 5 g/l, and most preferably at about 3 g/l. Urea concentrations in the fermentation medium are maintained within these ranges by the addition of a concentrated urea feed having a concentration of about 100 g/l.

The phosphate ($PO_4$) concentration in the fermentation medium is maintained at between about 0.03 g/l and about 0.3 g/l, more preferably between about 0.05 g/l and about 0.2 g/l, and most preferably at about 0.1 g/l. These concentrations are maintained by the addition of a concentrated potassium phosphate feed having a concentration of about 15.75 g/l. In addition to maintaining the phosphate concentration by adding potassium phosphate, sulfate concentrations are also maintained by adding magnesium sulfate to the fermentation medium by including magnesium sulfate in with the potassium phosphate feed. The magnesium sulfate in the feed has a concentration of about 11.37 g/l.

It should be recognized that the glucose, glycine, urea, phosphate, and sulfate feeds are added to the fermentation medium to achieve or maintain concentrations of these compounds in the fermentation medium. Accordingly, the concentrations of the additive feeds provided above are not critical or limiting to the present invention.

In the fermentation process of the present invention, a fermentation medium is prepared as described above. This medium is inoculated with a culture of riboflavin producing microorganisms, and in particular, strains of *C. famata*. To achieve successful fermentation, the inoculation must establish a minimum inoculation density. It is well recognized that fermentation processes require an initial minimum inoculation density for cell growth to proceed. While a minimum inoculation density in the present process has not been determined, it has been determined that successful fermentations can be achieved when the initial inoculation achieves optical densities of about 0.06 at 620 nm (1 cm cuvette). Inoculations providing higher initial densities are acceptable and will shorten the lag time prior to cell growth. At initial inoculation densities less than about 0.06, the lag time before cell growth initiates becomes longer and eventually a minimum inoculation density is reached which does not support growth.

After the fermentation medium is inoculated, the fermentation is allowed to proceed and concentrations of glucose, glycine, urea, phosphate and sulfate are monitored and maintained at concentrations discussed above. throughout the fermentation, the temperature of the medium should be maintained between about 29° C. and about 31° C., more preferably between about 29.5° C. and about 30.5° C., and most preferably between about 29.9° C. and about 30.1° C.

Dissolved oxygen in the fermentation medium must be maintained above levels to provide sufficient oxygen for utilization by the microorganisms. The dissolved oxygen content of he medium can be controlled by aeration and agitation. The dissolved oxygen content of the medium is preferably maintained above about 20% saturation and more preferably above about 40% saturation.

The pH of the medium is adjusted prior to inoculation. The pH of the medium can be adjusted by addition of various compounds known in the art, such as KOH, NaOH. This initial pH can be between about 6 and about 8, more preferably between about 6.5 and about 7.5, and most preferably between about 6.9 and 7.0. It has been recognized that during the fermentation, the pH of the medium drops dramatically at about the same time that a large increase in cell growth and riboflavin occur. These changes also coincide with the first demand for addition of phosphate, glucose, urea, and glycine. Typically, this acidification of the medium is observed between about 35 hours and about 55 hours, more typically between about 40 hours and about 50 hours, and most typically between about 42 hours and about 48 hours.

Typically, the pH of the medium drops to as low as 3.5, and more typically to about 3.9. During the remainder of the fermentation process, the pH typically remains between about 3.9 and about 6.0, more typically between about 3.9 and about 5.5, and most typically between about 3.9 and about 5.1. The pH of the medium then typically rises back to between about 5.0 and about 7.0 and more typically to between about 6.0 and about 7.0. When this rise in pH occurs cell growth generally stops.

The following experimental results are provided for purposes of illustration and are not intended to limit the scope of the invention.

EXAMPLE I

Roll Tube Riboflavin Assay

A colony of strain B was inoculated into a test tube containing 2.5 ml of Supplemented Defined Medium (see Table I-A) and allowed to grow at 30° C. with moderate agitation for 4 days. Test tubes with 2 ml of Supplemented Defined Medium were inoculated with 0.02 ml of the grown culture and incubated at 30° C. with moderate agitation for 7 days. The cultures were diluted by a factor of 500 and heated at 60° C.-70° C. for 40 minutes to dissolve riboflavin crystals. The absorbance at 445 nm of the dissolved solution was 0.245. This value is multiplied by 500 to correct for the dilution and multiplied by 31.3 to yield a riboflavin concentration of $3.8 \times 10^3$ mg/l or 3.8 g/l.

TABLE I-A

| Supplemented Defined Medium | |
|---|---|
| 4B | — |
| glycine | 0.23% |
| $CoCl_2$ | 1 ug/ml |
| $ZnCl_2$ | 10 ug/ml |
| $FeCl_3.6H_2O$ | 0.2 ug/ml |
| YMG Medium | 10% |
| sucrose | 6% |

EXAMPLE II

Strain Selection

Strain C was subjected to NTG mutagenesis at an NTG concentration of 0.10 mg/ml for 60 minutes at room temperature. These mutated cells were harvested, washed and suspended in physiological saline. The mutagenized cells were plated on Supplemented Defined Medium containing 750 µg/ml of 2-deoxyglucose. After 10 days, 125 colonies of resistant mutants were identified and tested for riboflavin production by the roll tube riboflavin assay described above. Strain D was the most productive mutant having a riboflavin production capacity of 1.58 g/l/7 days.

Strain D was subjected to NTG mutagenesis in the manner described above with an NTG concentration of 0.10 mg/ml for 60 minutes at room temperature. The treated cells were harvested, washed and suspended in equal volumes of physiological saline. This culture was plated on Supplemented Defined Medium containing 2.23 percent glycine to provide sufficient substrate for riboflavin synthesis and $FeCl_3 \cdot 6H_2O$ at a concentration of 5 µg/ml. After 10 days of incubation at 30° C., 25 colonies of resistant mutants were identified and tested for riboflavin synthesis by the roll tube riboflavin assay described above. Mutant Strain E was the highest riboflavin producing strain with a riboflavin production capacity of 1.70 g/l/7 days.

Strain E was subjected to NTG mutagenesis at an NTG concentration of 0.10 mg/ml for 60 minutes of incubation at room temperature. The treated cells were harvested, washed and suspended in equal volumes of physiological saline. A depleted medium was prepared by growing Strain E in Supplemented Defined Medium at a temperature of 30° C. with agitation for 3 weeks. The cells were removed from this culture by centrifugation and filtration with a 0.5 micron membrane filter. Sucrose (6 percent), glycine (0.23 percent), and agar (2 percent) were added to the supernatant. The mutated culture of strain E was plated on this medium and incubated at 30° C. for 10 days. 35 colonies having a yellow color were identified and tested for riboflavin production by the roll tube riboflavin assay. Strain A was derived from this selection procedure and has a riboflavin production capacity of 2.5 g/l/7 days.

Strain A was subjected to NTG mutagenesis at a concentration of 0.10 mg/ml for 60 minutes of incubation at room temperature. The treated cells were harvested, washed and suspended in equal volumes of physiological saline.

A depleted media was prepared by growing non-mutagenized strain A cells in medium as described in Table 3 for 10 days in 450 liter fermenter at 30° C. with agitation. Cells were removed from this culture by ultra-filtration. A solid selection medium was prepared with 50 percent of the liquid volume being the cell-free depleted medium and the remaining 50 percent of the liquid volume being water. The mutagenized Strain A cells were plated on this medium and incubated for 10 days at 30° C. Sixty colonies of resistant mutants were identified and tested for riboflavin production. Strain F was the highest riboflavin producer from this process having a riboflavin production capacity of 3.4 g/l/7 days in the roll tube riboflavin assay.

Strain F was subjected to NTG mutagenesis at an NTG concentration of 0.10 mg/ml for 60 minutes of incubation at room temperature. The treated cells were harvested, washed and suspended in physiological saline. These cells were subjected to selection on Supplemented Defined Medium containing 100 µg/ml tubercidin. After incubation for 10 days at 30° C., 25 colonies of viable strains were identified and tested for riboflavin production. Strain B was the most flavinogenic strain, having a riboflavin production capacity of 3.8 g/l/7 days.

Strain A was also the starting population for a second selection process. A culture of strain A was subjected to NTG mutagenesis at a concentration of 0.10 mg/ml for 60 minutes of incubation at room temperature. The treated cells were harvested, washed and suspended in physiological saline. This culture was subjected to tubercidin selection by plating the mutated cells on Supplemented Defined Medium containing 100 µg/ml tubercidin. After 10 days of incubation at 30° C., 20 viable colonies were selected and tested for riboflavin production. Strain G was the was the most flavinogenic, producing 2.9 g/l/7 days.

Strain G was the starting population for an ultraviolet light sensitivity selection process. Strain G was subjected to NTG mutagenesis at a concentration of 0.10 mg/ml for 60 minutes of incubation at room temperature. The treated cells were harvested, washed and suspended in physiological saline. This cell suspension was diluted by $1:10^4$ to yield a cell concentration of 1000 cells/ml. 0.1 ml of cell suspension was plated on YMG Medium and incubated for 3 days at 30° C. At this point colonies were visible and were replicated twice to fresh agar plates. The first replica was exposed open-faced to 17 $J/m^2$ of ultraviolet light. The irradiated plate was incubated in the dark along with the non-irradiated replica plate at 30° C. for 4 days to allow for colony formation. The irradiated and non-irradiated plates were compared to identify non-viable colonies indicating ultraviolet sensitive mutants. These mutants were identified on the non-irradiated plate and assayed for riboflavin production. 14 colonies were identified by this method and the highest producing mutant was Strain H, which can produce 3.1 g/l of riboflavin in 7 days.

EXAMPLE III

Riboflavin production Test Run No. 1 was conducted in a 14 liter fermentor. The composition of the fermentation medium for this run is provided in Table 3. All medium constituents, except glucose, were filter sterilized into the fermentation tank prior to introduction to the rest of the medium. Glucose was autoclaved for 30 minutes at 121° C. and 15 psi. The pH of the medium was adjusted to 6.9–7.0 prior to inoculation. The fermentation tank was inoculated with a oulture of strain A to provide an initial optional density of 0.06 at 620 nm (1 cm cuvette).

Test Run No. 1 was conducted for 240 hours. During this time, the optical density at 620 nm, riboflavin, pH, temperature, glycine, urea, phosphate, and glucose were monitored. The results of this fermentation are provided in Tables III-A and III-B. A final riboflavin concentration of 15.93 g/l was obtained in 240 hours.

TABLE III-A

| Time (h) | Optical Density (620 nm) | Riboflavin (g/l) | pH | Temperature (°C.) |
|---|---|---|---|---|
| 0 | 0.06 | 0.000 | 6.92 | 30 |
| 26.5 | 1.41 | 0.018 | 6.01 | 30 |
| 45.5 | 25.25 | 0.465 | 3.97 | 29.7 |

TABLE III-A-continued

| Time (h) | Optical Density (620 nm) | Riboflavin (g/l) | pH | Temperature (°C.) |
|---|---|---|---|---|
| 75.5 | 105.0 | 3.25 | 4.4 | 29.7 |
| 103.0 | 129.0 | 6.4 | 4.7 | 29.6 |
| 127.0 | 121.0 | 8.01 | 5.06 | 29.6 |
| 143.5 | 122.0 | 9.17 | 5.02 | 29.5 |
| 174.5 | 109.0 | 10.94 | 4.74 | 29.7 |
| 190.5 | 142.0 | 12.96 | 4.35 | 29.6 |
| 204.0 | 152.0 | 13.62 | 4.25 | 29.7 |
| 240.0 | 169 | 15.93 | 3.92 | 29.4 |

TABLE III-B

| Time (h) | Glycine (g/l) | Urea (g/l) | Phosphate (g/l) | Glucose (g/l) |
|---|---|---|---|---|
| 0 | 4.43 | 4.52 | 0.650 | 74.8 |
| 32 | 4.40 | 4.99 | 0.587 | 80.3 |
| 45.5 | 4.13 | 3.84 | 0.358 | 57.2 |
| 56 | 3.06 | 3.30 | 0.087 | 29.9 |
| 70 | 4.00 | 3.62 | 0.298 | 32.1 |
| 85 | 4.44 | 3.48 | 0.276 | 31.2 |
| 103 | 4.09 | 2.96 | 0.268 | 40.3 |
| 127.5 | 4.00 | 3.77 | 0.330 | 41.9 |
| 143.5 | 4.32 | 1.31 | 0.183 | 46.7 |
| 167.5 | 3.15 | 5.14 | 0.337 | 50.9 |
| 190.5 | 2.70 | 5.93 | 0.128 | 33.4 |
| 215.5 | 2.40 | 5.86 | 0.101 | 35.3 |
| 240.0 | 2.0 | 6.51 | 0.175 | 34.3 |

EXAMPLE IV

Riboflavin production Test Run No. 2 was conducted in a 450 liter fermentation tank, and was run for 200 hours. The fermentation medium and inoculation was prepared in the same manner as for Example III. The results of this test run are provided in Table IV-A. A final riboflavin concentration of 21.0 g/l was achieved at the end of 200 hours in Test Run No. 2.

TABLE IV-A

| Time (h) | Optical Density (620 nm) | Riboflavin (g/l) | pH | Temperature (°C.) | Glycine (g/l) | Urea (g/l) | Glucose (g/l) |
|---|---|---|---|---|---|---|---|
| 0 | 0.06 | 0.0 | 6.95 | 30 | 5.2 | 4.2 | 68.8 |
| 40 | 25.0 | 0.0 | 4.60 | 30 | 4.0 | 2.4 | 47.8 |
| 60 | 50.0 | 2.5 | 5.40 | 30 | 6.8 | 3.4 | 32.2 |
| 80 | 150 | 6.0 | 5.2 | 30 | 6.7 | 4.4 | 43.0 |
| 100 | 175 | 9.0 | 5.9 | 30 | 7.5 | 6.5 | 47.9 |
| 140 | 225 | 15.0 | 5.0 | 30 | 7.0 | 7.7 | 44.5 |
| 200 | 210 | 21.0 | 5.3 | 30 | 7.0 | 6.3 | 47.2 |

EXAMPLE V

Riboflavin production Test Run No. 3 was conducted in a 450 liter fermentation tank and was run for 200 hours. The fermentation medium and inoculation was prepared in the same manner as for Example III. The results of this test are provided in Table V-A. A final riboflavin concentration of 16.0 g/l was achieved at the end of 200 hours in this test run.

TABLE V-A

| Time (h) | Optical Density (620 nm) | Riboflavin (g/l) | pH | Temperature (°C.) |
|---|---|---|---|---|
| 0 | 0.06 | 0.0 | 6.95 | 30 |
| 40 | 10.0 | 0.0 | 5.00 | 30 |
| 60 | 25.0 | 1.0 | 4.1 | 30 |
| 80 | 75.0 | 3.0 | 4.7 | 30 |
| 100 | 110 | 6.0 | 5.2 | 30 |
| 140 | 150 | 10.0 | 5.0 | 30 |
| 200 | 180 | 16.0 | 4.4 | 30 |

| Time (h) | Glycine (g/l) | Urea (g/l) | Phosphate (g/l) | Glucose (g/l) |
|---|---|---|---|---|
| 0 | — | 4.2 | 0.630 | 47.6 |
| 40 | — | 4.3 | 0.620 | 42.4 |
| 60 | — | 3.7 | 0.400 | 56.6 |
| 80 | 4.5 | 2.8 | 0.070 | 35.4 |
| 100 | 5.0 | 1.7 | 0.180 | 41.8 |
| 140 | 7.4 | 3.3 | 0.050 | 34.8 |
| 200 | 0.7 | 5.7 | 0.100 | 44.2 |

EXAMPLE VI

A series of test runs were conducted holding all conditions constant, except that $FeSO_4 \cdot 7H_2O$ concentration was varied with concentrations of 0 mg/l, 1 mg/l, 2 mg/l, and 3 mg/l. The fermentations were conducted in 150 liter pilot scale tanks using the fermentation medium as provided in Table 3. Additionally, the following compositions were added to the fermentation medium.

| Composition | Concentration (g/l) |
|---|---|
| Yeast extract | 1.04 |
| Malt extract | 1.04 |
| Peptone | 1.73 |

Strain A was used for the fermentation runs. Cell growth and riboflavin production were monitored during the fermentation. Table VI-A provides the results of cell growth throughout the four fermentations. Table VI-B provides the results of riboflavin production for the four fermentations. Table VI-C provides the final ratios of riboflavin production to cell growth for each of the four fermentations. As seen in Table VI-C, at higher $FeSO_4 \cdot 7H_2O$ concentrations, the amount of riboflavin produced per cell weight increases. While substantial increases in this ratio are achieved at 1 mg/l and 2 mg/l, the increase between 2 mg/l and 3 mg/l is minimal.

TABLE VI-A

| Time (h) | Cell Weight (g/l) ($FeSO_4 \cdot 7H_2O$) = 0) | Cell Weight (g/l) ($FeSO_4 \cdot 7H_2O$) = 1 mg/l) | Cell Weight (g/l) ($FeSO_4 \cdot 7H_2O$) = 2 mg/l) | Cell Weight (g/l) ($FeSO_4 \cdot 7H_2O$) = 3 mg/l) |
|---|---|---|---|---|
| 38 | — | — | 4.8 | 5.3 |
| 62 | — | — | 10.1 | 13.2 |
| 86 | 4.8 | 9.6 | 14.8 | 18.9 |
| 110 | 9.9 | 14.0 | 20.7 | 22.4 |
| 134 | 11.2 | 21.9 | 23.3 | 26 |
| 164 | 15.9 | 23.2 | 26.5 | 28.3 |

TABLE VI-B

| Time (h) | Riboflavin (g/l) (FeSO$_4$.7H$_2$O) = 0 | Riboflavin (g/l) (FeSO$_4$.7H$_2$O) = 1 mg/l | Riboflavin (g/l) (FeSO$_4$.7H$_2$O) = 2 mg/l | Riboflavin (g/l) (FeSO$_4$.7H$_2$O) = 3 mg/l |
|---|---|---|---|---|
| 86 | 1.37 | 2.54 | 4.12 | 5.26 |
| 110 | 2.19 | 4.05 | 5.72 | 7.13 |
| 134 | 2.13 | 5.03 | 8.10 | 9.32 |
| 164 | 3.19 | 6.52 | 9.34 | 10.20 |

TABLE VI-C

Riboflavin Produced Per Unit Growth of Strain A

| FeSO$_4$.7H$_2$O (mg/l) | 0 | 1 | 2 | 3 |
|---|---|---|---|---|
| riboflavin (g/l) / cell weight (g/l) | 0.20 | 0.28 | 0.35 | 0.36 |

EXAMPLE VII

A series of test runs were conducted to determine the effect of depleted media on Strain A. The fermentations were conducted for 90 hours in 14 liter fermentors using the fermentation medium as provided in Table 3. All conditions were identical except that for each of the test runs depleted media was used for a different portion of the liquid constituting the fermentation medium. The first test run had no depleted medium, the second had 20%, the third had 40%, the fourth had 50% and the fifth had 80%. The riboflavin production for each of the test runs at various time intervals throughout the fermentation run are shown below in Table VII-A.

TABLE VII-A

Effect on Riboflavin Production (g/l) of Depleted Media

| Hours | 0% dep. med. | 20% dep. med. | 40% dep. med. | 60% dep. med | 80% dep. med. |
|---|---|---|---|---|---|
| 42 | 0.5 | 1.1 | 0.6 | 0.3 | 0.0 |
| 58 | 1.3 | 2.4 | 1.4 | 0.6 | 0.4 |
| 74 | 3.1 | 4.5 | 2.6 | 1.2 | 0.7 |
| 89 | 4.9 | 6.1 | 4.6 | 2.6 | 1.9 |

An initial stimulation of riboflavin production is observed at 20% depleted medium. However, at increasing concentrations of depleted medium, riboflavin production is increasingly inhibited.

While various embodiments of the present invention have been described in detail, it is apparent that modifications and adaptations of those embodiments will occur to those skilled in the art. However, it is to be expressly understood that such modifications and adaptations are within the scope of the present invention, as set forth in the following claims.

What is claimed is:

1. A *Candida famata* strain, having all the identifying characteristics of strain ATCC 20849, and mutants thereof, wherein such strain and mutants produce at least about 10 grams of riboflavin per liter of fermentation medium in six days.

2. A *Candida famata* strain, having all the identifying characteristics of strain ATCC 20850, and mutants thereof, wherein said strains and mutants product at least about 10 grams of riboflavin per liter of fermentation medium in six days.

* * * * *